(12) United States Patent
Welch et al.

(10) Patent No.: US 10,252,957 B2
(45) Date of Patent: Apr. 9, 2019

(54) OFFGAS STREAM DIRECT CONTACT CONDENSER

(71) Applicant: Fina Technology, Inc., Houston, TX (US)

(72) Inventors: Vincent A Welch, Medway, MA (US); James R Butler, Spicewood, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 164 days.

(21) Appl. No.: 15/486,043

(22) Filed: Apr. 12, 2017

(65) Prior Publication Data

US 2017/0217857 A1    Aug. 3, 2017

Related U.S. Application Data

(62) Division of application No. 14/635,041, filed on Mar. 2, 2015, now Pat. No. 9,650,317, which is a division of application No. 12/564,062, filed on Sep. 22, 2009, now Pat. No. 8,999,257.

(51) Int. Cl.

| | |
|---|---|
| *C07C 5/327* | (2006.01) |
| *C07C 5/333* | (2006.01) |
| *C07C 7/00* | (2006.01) |
| *C07C 7/09* | (2006.01) |
| *C01B 3/32* | (2006.01) |
| *C01B 3/50* | (2006.01) |
| *F25J 3/06* | (2006.01) |
| *C01B 3/24* | (2006.01) |
| *F28B 3/00* | (2006.01) |
| *F28B 9/06* | (2006.01) |

(52) U.S. Cl.
CPC .................. *C07C 7/09* (2013.01); *C01B 3/24* (2013.01); *C01B 3/323* (2013.01); *C01B 3/50* (2013.01); *C01B 3/506* (2013.01); *C07C 5/333* (2013.01); *F25J 3/063* (2013.01); *F25J 3/0655* (2013.01); *F28B 3/00* (2013.01); *F28B 9/06* (2013.01); *C01B 2203/0233* (2013.01); *C01B 2203/0266* (2013.01); *C01B 2203/04* (2013.01); *C01B 2203/048* (2013.01); *C01B 2203/0495* (2013.01); *Y10S 585/921* (2013.01)

(58) Field of Classification Search
CPC ............ C07C 5/327; C07C 5/333; C07C 7/00
USPC ................... 585/804, 806, 440, 441
See application file for complete search history.

(56) References Cited

U.S. PATENT DOCUMENTS 4,288,234 A  *  9/1981  Cox .................... B01D 53/1487
                                                585/805

FOREIGN PATENT DOCUMENTS

WO          0020375 A1    4/2000

OTHER PUBLICATIONS

Office Action issued in Korean Application No. 2012-7005758, dated Apr. 28, 2017, 13 pages.

* cited by examiner

*Primary Examiner* — Thuan D Dang
(74) *Attorney, Agent, or Firm* — Albert Shung

(57) ABSTRACT

Methods and systems for the dehydrogenation of hydrocarbons include a direct contact condenser to remove compounds from an offgas process stream. The reduction of compounds can decrease duty on the offgas compressor by removing steam and aromatics from the offgas. The dehydrogenation reaction system can be applicable for reactions such as the dehydrogenation of ethylbenzene to produce styrene, the dehydrogenation of isoamiline to produce isoprene, or the dehydrogenation of n-pentene to produce piperylene.

10 Claims, 1 Drawing Sheet

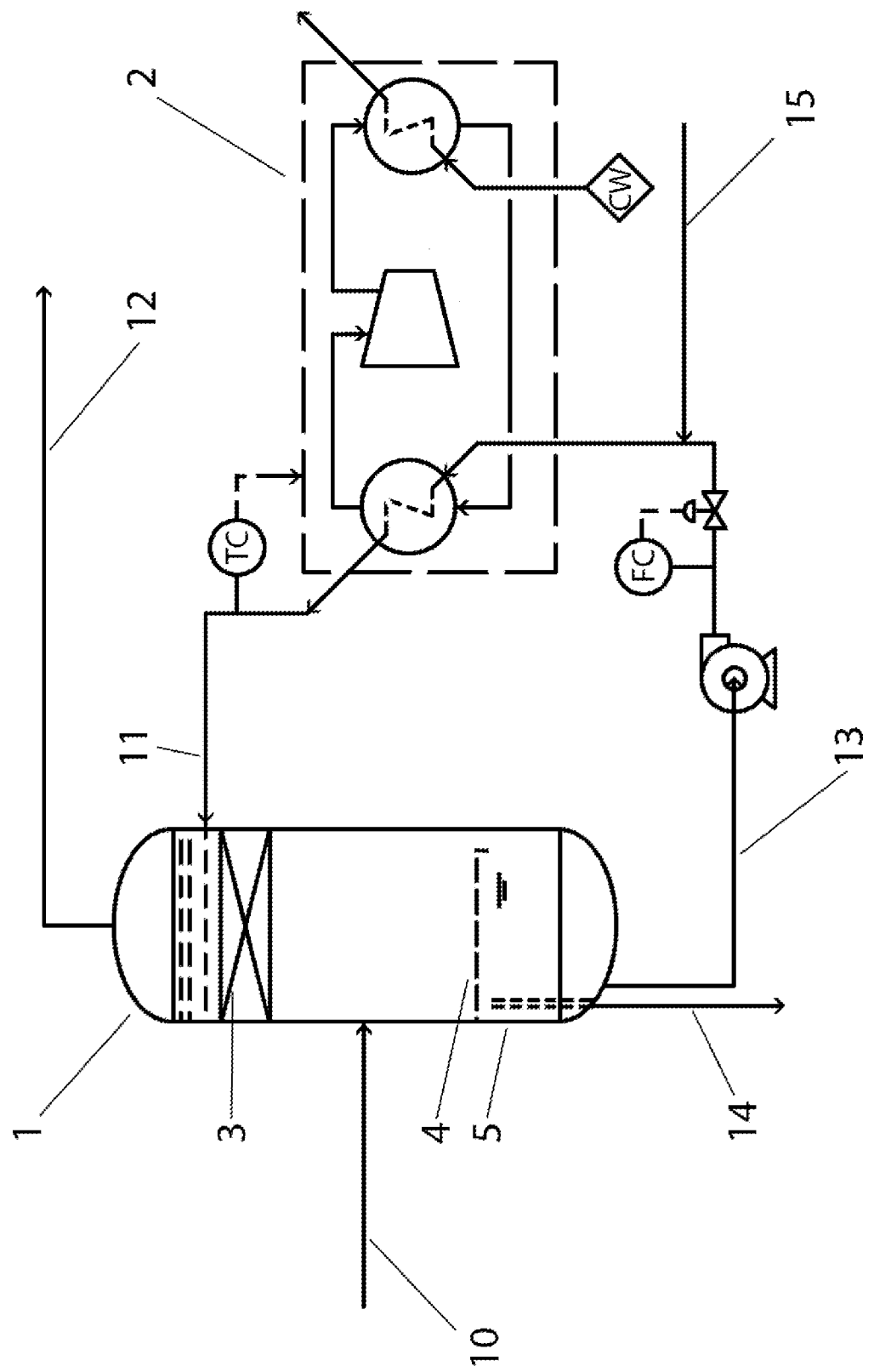

OFFGAS STREAM DIRECT CONTACT CONDENSER

CROSS-REFERENCE TO RELATED APPLICATIONS

This application is a Divisional of U.S. patent application Ser. No. 14/635,041, filed on Mar. 2, 2015, which is Divisional of U.S. patent application Ser. No. 12/564,062, now issued U.S. Pat. No. 8,999,257, filed on Sep. 22, 2009.

FIELD

The present invention generally relates to the processing of offgas from a dehydrogenation reactor system.

BACKGROUND

Styrene monomer is the monomer from which the polymer polystyrene and co-polymers of polystyrene, such as high impact polystyrene and acrylonitrile butadiene styrene, are produced. Polymers of styrene are common and valuable plastics that can be used in the production of items from electronics casing to toys to disposable plates and cups. The chemical formula of styrene monomer is $C_6H_5C_2H_3$, and its structure consists of a benzene ring with an attached ethylene group. Styrene is generally produced via the dehydrogenation of ethylbenzene. Ethylbenzene has the chemical formula of $C_6H_5C_2H_5$, and its structure consists of a benzene ring with an attached ethyl group.

Ethylbenzene dehydrogenation takes place in a dehydrogenation reactor system, which comprises a series of dehydrogenation reaction chambers and downstream processing equipment. Superheated steam and ethylbenzene enter the reaction chambers, such as in a steam to hydrocarbon molar ratio of at least 4:1, where a dehydrogenation catalyst catalyzes the conversion of ethylbenzene to styrene. The reaction is generally run at a temperature of around 300° C. to 650° C. and atmospheric to sub-atmospheric pressure, such as around 5 to 20 psia. The mechanism for the dehydrogenation reaction involves the loss of two hydrogen atoms from the ethyl group to form a carbon-carbon double bond. Thus, the chemicals exiting the series of reaction chambers generally comprise styrene, hydrogen gas, and steam, as well as unreacted ethylbenzene and other compounds, which can be referred to as styrene offgas.

From the reaction chambers, the products are cooled and separated into offgas (also known as vent gas), condensate, and organic compounds such as aromatics. The styrene offgas is generally fed to a compressor, and then cooled and condensed to obtain hydrogen-rich gas, which can be used for a variety of purposes, such as providing a fuel source for the superheating of the steam used in the reactor system.

The offgas compressor provides the vacuum that allows the dehydrogenation reaction to take place at sub-atmospheric or low atmospheric pressures. The use of lower pressure increases the duty of the vent gas compressor, due to the increased suction volume as a result of pulling in greater amounts of water and organics/aromatics vapors along with the hydrogen gas. Styrene offgas can contain hydrogen, water vapor, methane, ethylene, carbon monoxide and carbon dioxide, as well as aromatics such as ethylbenzene vapor and toluene, benzene, and styrene vapor. Particularly problematic is the presence of styrene, which readily polymerizes upon exposure to high temperatures or long residence times, such as those encountered in the offgas process stream.

Thus, a need exists for an economic solution for the removal of organic compounds, water vapor and other detrimental compounds from a dehydrogenation offgas stream, such as a styrene offgas stream.

SUMMARY

The present invention, in its many embodiments, involves the use of a direct contact condenser in an offgas stream, upstream of an offgas compressor for the removal of compounds that can negatively increase the duty of the compressor.

The direct contact condenser can be employed in the processing of offgas streams of many reaction systems, particularly dehydrogenation reaction systems. One reaction system for which the present invention is suitable is an ethylbenzene reaction system that produces styrene. The offgas of dehydrogenation reaction systems can contain organic compounds and steam, which can increase the duty on the offgas compressor and lower its vacuum suction. The direct contact condenser can largely remove steam and organic compounds from the offgas stream prior to its entering the offgas compressor. Each of the embodiments listed herein can be taken alone or in combination with other embodiments and are not limiting.

In one embodiment, the direct contact condenser is installed in a knock out drum of a styrene offgas processing stream. In an embodiment, the cooling medium used in the direct contact condenser comprises chilled water. In another embodiment, the cooling medium comprises chilled water as well as ethylbenzene. In an embodiment, the direct contact condenser has one theoretical stage of separation. In another embodiment, the direct contact condenser has more than one theoretical stage of separation.

In an embodiment, the invention is for a method of removing organic compounds and steam from dehydrogenation reactor offgas, comprising the steps of feeding the offgas into a direct contact condenser; contacting the offgas with a cooling medium; collecting the condensed organic compounds and steam at the bottom of the condenser; and collecting the noncondensable vapors at the top of the condenser. The method can further comprise the steps of sending the condensed organic compounds and steam to the main process separator of the dehydrogenation reaction system and sending the noncondensable vapors to an offgas compressor. In an embodiment, the dehydrogenation reaction system is for the dehydrogenation of ethylbenzene to produce styrene, and the condensing of organic compounds including styrene and ethylbenzene.

The method can include supplying steam to the reaction in a steam to hydrocarbon molar ratio of at least 4:1 and operating the dehydrogenation reaction at a temperature of at least 300° C.

An embodiment of the present invention is a dehydrogenation reaction system including a dehydrogenation reactor capable of the dehydrogenation of hydrocarbons. An offgas compressor capable of removing vapor from the dehydrogenation reactor system compresses an offgas stream and maintains the pressure within the dehydrogenation reactor system. A direct contact condenser is located between the reactor and the offgas compressor that is capable of contacting the offgas stream with a quench stream prior to the offgas stream exiting the condenser and entering the offgas compressor. The quench stream cools the offgas stream and enables the condensation of organic compounds and steam contained within the offgas stream.

The condenser can be installed in an offgas compressor suction knock out drum. The system can be used for the dehydrogenation of ethylbenzene to produce styrene or optionally for the dehydrogenation of isoamiline to produce isoprene. The offgas can contain steam, styrene, and non-polymerizable organic compounds such as aromatics, all of which are largely removed by the condenser. The quench stream can be chilled water and can include ethylbenzene. The condenser can have one or more theoretical stages of separation.

An alternate embodiment is a method for the dehydrogenation of hydrocarbons that includes contacting a hydrocarbon feedstock with a dehydrogenation catalyst within a reactor under reaction conditions effective to dehydrogenate at least a portion of said hydrocarbon feedstock. An offgas stream is removed that includes hydrogen produced from the reactor. A direct contact condenser capable of circulating a cooling medium and contacting the offgas stream with the cooling medium is used to cool the offgas stream and enable the condensation of organic compounds and steam from the offgas stream. A cooled offgas stream having a reduced content of organic compounds and steam is removed from the direct contact condenser.

The dehydrogenation reactor can be operated at reduced pressure conditions wherein substantially all of the hydrocarbons are in a vapor phase and a vapor product can be recovered from the dehydrogenation reactor that includes dehydrogenated product.

The cooling medium can be chilled water and can include ethylbenzene. The condensed compounds can include styrene, ethylbenzene, toluene, and benzene. The condensed compounds can be blended into the hydrocarbon feedstock. The cooled offgas stream can be compressed in an offgas compressor capable of maintaining the pressure within the reactor.

BRIEF DESCRIPTION OF DRAWINGS

FIG. 1 illustrates an embodiment of a direct contact condenser installed in a styrene offgas process stream.

DETAILED DESCRIPTION

The present invention in its many embodiments involves the installation of a direct contact condenser in an offgas stream, upstream of an offgas compressor. The direct contact condenser can remove organic compounds and aqueous condensate from the offgas stream to lower the duty on the compressor, while maintaining economic feasibility.

Direct contact condensers are known in the art. A direct contact condenser can achieve a relatively greater amount of heat transfer between the cooling medium and the vapor because the cooling medium and the vapor contact each other directly, with no intermediate surfaces to absorb a portion of the heat transfer. In conventional heat exchangers, heat transfer occurs between tubing wall surfaces as well as between the cooling medium and the vapor, plus the temperature can rise in the cooling water circulation. Thus, conventional heat exchangers incur greater power requirements on the refrigeration unit, making direct contact condensers more economical for certain applications, such as offgas processing, as in styrene offgas processing. The type of direct contact condenser used in the present invention can be any known in the art, including jet, spray and barometric condensers.

In one embodiment, the direct contact condenser is of the type shown in FIG. 1. The apparatus for the direct contact condenser can be installed in the offgas compressor suction knock out drum, or KO drum 1, and a conventional refrigeration unit 2 is added. The apparatus inside the KO drum 1 includes quench packing 3, a collector baffle 4, and an overflow pipe 5. Styrene offgas leaving the main styrene process separator travels via line 10 to an inlet in the direct contact condenser, in this case contained within the KO drum 1. Cooling water that has been chilled in the refrigeration unit 2 enters the KO drum 1 via line 11 and contacts the offgas. Ethylbenzene can optionally be added to the cooling water by entering the refrigeration unit 2 via line 15. In the contacting region the cooling water heats up while cooling the offgas. Upon contacting the chilled water, aromatics vapor and steam (water vapor) present in the offgas can condense and travel toward the bottom of the KO drum 1. Noncondensables, comprising hydrogen gas, rise and leave the KO drum 1 at the top, and then travel via line 12 to a vacuum compressor (not shown), where they are processed in the normal fashion. Condensables, which includes recycle water, condensed water from steam, and aromatics liquids, fall downward by gravity and collect on the collector baffle 4. From an opening in the baffle 4, the combined liquids flow first down and then sideways across the bottom of the KO drum 1 to effect gravity separation of the lighter aromatics liquids from the heavier water. The decanted aromatics liquids and a water flow substantially equal to the condensed offgas stream are directed through the overflow pipe 5. They leave the condenser via line 14 and return to the main styrene process separator (not shown). The circulating cooling water can exit the KO drum 1 via line 13 for return to the refrigeration unit 2.

FIG. 1 discloses a particular embodiment of the present invention, and many alterations are possible without departing from the scope of the invention. For instance, the direct contact condenser is variable in terms of its operating parameters, including temperature, pressure, and flow rate. The percentage of organic compounds removed by the direct contact condenser can also vary, depending on process needs and economics. Furthermore, the direct contact condenser can be designed to have more than one theoretical separation stage in the quench contacting region, to effect a greater separation of organic compounds from the offgas. A greater number of separation stages can be implemented by increasing the number of inlets for cooling water, for example.

This invention can also be applied towards dehydrogenation reaction systems with reactants other than ethylbenzene. Various vinyl aromatic compounds can be prepared by the catalytic dehydrogenation of corresponding $C_2$ or $C_3$ alkyl aromatic compounds. Such reactions include the catalytic dehydrogenation of monoalkyl or polyalkyl aromatics, such as diethylbenzene, or the dehydrogenation of alkyl substituted polynuclear aromatic compounds, such as ethylnaphthalene. As an example, n-propyl benzene can be dehydrogenated to produce beta methyl styrene, and cumene can be dehydrogenated to produce alpha methyl styrene. Other reactions include but are not limited to the dehydrogenation of ethyl toluene to produce vinyl toluene and the dehydrogenation of diethylbenzene to produce divinylbenzene. In another example isoprene can be produced by the dehydrogenation reaction of isoamylene or piperylene from dehydrogenation of n-pentene. All of these reactions produce hydrogen offgas that can be sent to a vacuum compressor. Just as in the dehydrogenation of ethylbenzene, the offgas can contain organic vapors that can be harmful to the vacuum compressor. Thus, these reactions can be benefited by the use of a direct contact condenser in the offgas process stream, according to the present invention.

In one embodiment, the invention is a method for the removal of organic compounds and steam from the offgas of a dehydrogenation reaction system. The method comprises feeding the offgas into a direct contact condenser, upstream of an offgas compressor. The method further comprises feeding a cooling medium, such as water or a combination of water and ethylbenzene, into the direct contact condenser, in which the cooling medium and the offgas form a contact zone for heat transfer. The method further comprises collecting condensed steam and organic compounds at the bottom of the direct contact condenser and sending them back to a main process separator of the dehydrogenation reaction system. The method further comprises collecting the noncondensable vapors, which comprise hydrogen and other gasses, at the top of the direct contact condenser and sending them on to the offgas compressor.

In embodiments the method condenses the majority of the organic compounds and steam from the offgas stream. In alternate embodiments the method condenses at least 60%, at least 70%, at least 80%, at least 90%, at least 95% of the organic compounds and steam from the offgas stream.

The method can include supplying steam to the reaction in a steam to hydrocarbon molar ratio of at least 4:1, optionally at least 5:1, optionally at least 8:1, optionally at least 10:1. The dehydrogenation reaction can be operated at a temperature of at least 300° C., optionally at least 350° C., optionally at least 400° C., optionally at least 450° C., optionally at least 500° C. The dehydrogenation reaction can be operated at any suitable pressure, such as above atmospheric to sub-atmospheric pressure. In embodiments the reaction can be operated from 2 to 30 psia, optionally from 5 to 20 psia.

In an embodiment, the dehydrogenation reaction system is for the dehydrogenation of ethylbenzene to produce styrene, and the condensing of organic compounds including styrene and ethylbenzene.

The present invention in its many embodiments can yield several potential benefits to the dehydrogenation reaction system. One benefit can be the reduction of organic compounds, such as aromatics entering the hydrogen offgas compressor, such that the duty on the compressor can be decreased and the dehydrogenation reaction system can be operated at a lower, and more economical, pressure.

Another benefit of the direct contact condenser of the present invention can be the preferential condensation of styrene monomer aromatics compared to the other non-polymerizable organic compounds such as aromatics, including ethylbenzene, toluene, and benzene, that are present in the hydrogen offgas. Styrene monomer in the liquid form tends to polymerize and foul the equipment in the vacuum compressor. Styrene polymerization is favored by higher temperatures and low dilution by non-polymerizable organic compounds. The direct contact condenser can promote preferential condensation of styrene monomer from the offgas by operating at a cooler quench temperature, by including added ethylbenzene in the cooling water, and by having multiple theoretical separation stages in the quench contacting area.

Another benefit of the direct contact condenser of the present invention can be a relatively low pressure drop of the hydrogen offgas, compared to conventional heat exchangers. A relatively low pressure drop can decrease the compression duty by requiring less compressor suction pressure.

Another benefit of the direct contact condenser of the present invention can be relatively low capital cost. The refrigeration system can be a lower cost for reasons already noted. The refrigeration system is the major cost item in either a direct contact or heat exchanger offgas chilling system. The direct contact condenser's other capital costs can also be lower than those of the conventional heat exchanger condenser.

The term "alkyl" refers to a functional group or side-chain that consists solely of single-bonded carbon and hydrogen atoms, for example a methyl or ethyl group.

The term "aromatics" refers to those chemicals consisting essentially of one or more benzene rings, which are optionally substituted. With reference to the dehydrogenation of ethylbenzene, aromatics in the styrene offgas can include styrene, ethylbenzene, benzene, toluene, and possibly others.

The term "condensables" refers to those chemicals that condense when processed through a heat exchanger and enter a liquid state. The term "condensate" refers more specifically to water that leaves a heat exchanger in the liquid state. With reference to a direct contact condenser, according to the present invention, the condensate can comprise recycle water that originated as cooling water as well as water that originated as steam in the offgas.

The term "direct contact condenser" refers to a type of heat exchanger wherein the cooling medium and the vapor are in direct contact.

The term "noncondensables" refers to those chemicals that do not condense when processed through a heat exchanger, and hence, remain in the vapor state.

The term "offgas" as used herein refers to products of a dehydrogenation reaction that leave the main process separator in a vapor state.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method for removing aromatics and steam from a dehydrogenation reactor offgas, comprising:
    feeding a dehydrogenation offgas stream comprising styrene and steam from an ethylbenzene reaction system for production of styrene into a direct contact condenser;
    contacting the offgas stream with a cooling medium comprising chilled water and ethylbenzene;
    condensing organic compounds including styrene and steam from the offgas stream to form condensed organic compounds and water;
    removing the condensed organic compounds and water from the direct contact condenser;
    removing noncondensable vapors from the direct contact condenser; and
    sending the noncondensable vapors to an offgas compressor to compress the noncondensable vapors.

2. The method of claim 1, wherein the condensed organic compounds comprise one or more of styrene, ethylbenzene, toluene, and benzene.

3. The method of claim 1, further comprising sending the condensed organic compounds to a main process separator.

4. The method of claim 1, wherein quench packing is located within an interior top section of the direct contact condenser.

5. The method of claim 4, wherein the direct contact condenser is located downstream of a styrene offgas feed line and is in fluid contact with the styrene offgas feed line, wherein the styrene offgas feed line is downstream of a dehydrogenation reactor;
  wherein a cooling medium inlet line is in fluid contact with the interior top section of the direct contact condenser; and
  wherein a collector baffle is located within an interior bottom section of the direct contact condenser, and wherein a decanted aromatics outlet line is in fluid connection with the interior bottom section of the direct contact condenser.

6. The method of claim 1, wherein a noncondensable vapors outlet line is in fluid connection with an interior top section of the direct contact condenser, and wherein a vacuum compressor is in fluid connection with the noncondensable vapors outlet line.

7. The method of claim 6, wherein the direct contact condenser is in fluid contact with and downstream of a styrene offgas feed line, wherein the styrene offgas feed line is downstream of a dehydrogenation reactor;
  wherein a cooling medium inlet line is in fluid contact with the interior top section of the direct contact condenser;
  wherein a collector baffle is located within an interior bottom section of the direct contact condenser, and wherein a decanted aromatics outlet line is in fluid connection with the interior bottom section of the direct contact condenser.

8. The method of claim 1, wherein the direct contact condenser has an interior top section and an interior bottom section, wherein the direct contact condenser is in fluid contact with a styrene offgas feed line, wherein a noncondensable vapors outlet line is in fluid connection with the interior top section of the direct contact condenser, wherein a vacuum compressor is in fluid connection with the noncondensable vapors outlet line, and wherein the direct contact condenser is located between the vacuum compressor and a dehydrogenation reactor.

9. The method of claim 8, wherein the direct contact condenser comprises:
  a cooling medium inlet line in fluid contact with the interior top section of the direct contact condenser;
  a collector baffle located within the interior bottom section of the direct contact condenser;
  a decanted aromatics outlet line in fluid connection with the interior bottom section of the direct contact condenser;
  an overflow pipe adapted to conduct liquids from the collector baffle to the decanted aromatics outlet line;
  quench packing, wherein the quench packing is located within the interior top section of the direct contact condenser;
  a cooling medium outlet line in fluid connection with the bottom section of the direct contact condenser;
  a refrigeration unit in fluid connection with the cooling medium outlet line and the cooling medium inlet line; and
  an ethylbenzene line adapted to inject ethylbenzene into the cooling medium outlet line.

10. The method of claim 1, wherein the direct contact condenser is located between a vacuum compressor and a dehydrogenation reactor.

* * * * *